United States Patent [19]

Okuda et al.

[11] 4,243,321
[45] Jan. 6, 1981

[54] HANDY REFRACTOMETER

[75] Inventors: Minoru Okuda, Akatsukashinmachi; Mikio Ito, Yokohama, both of Japan

[73] Assignee: Nippon Kogaku K.K., Tokyo, Japan

[21] Appl. No.: 69,925

[22] Filed: Aug. 27, 1979

[51] Int. Cl.³ .......................................... G01N 21/43
[52] U.S. Cl. ................................................. 356/135
[58] Field of Search ...................... 356/128, 135, 136

[56] References Cited
U.S. PATENT DOCUMENTS

| | | | |
|---|---|---|---|
| 2,729,137 | 1/1956 | Forrest | 356/137 |
| 3,778,165 | 12/1973 | Grubb et al. | 356/128 |

Primary Examiner—John K. Corbin
Assistant Examiner—Bruce Y. Arnold
Attorney, Agent, or Firm—Fitzpatrick, Cella, Harper & Scinto

[57] ABSTRACT

This specification discloses a refractometer of the type in which a sample is introduced onto a prism by a pump device, whereafter the sample is illuminated so that the critical angle of the total reflection determined by the refractive indices of the sample and the prism is measured. The refractometer comprises a substantially rectangular parallelopiped frame member, a cylinder provided within the frame member and having a piston slidably disposed at the upper end thereof, an observation lens barrel disposed laterally within the frame member and in juxtaposed relationship with the cylinder, prism holding means, and reflector means for directing a light beam emergent from the prism to the observation lens barrel.

7 Claims, 6 Drawing Figures

FIG. 1
FIG. 2
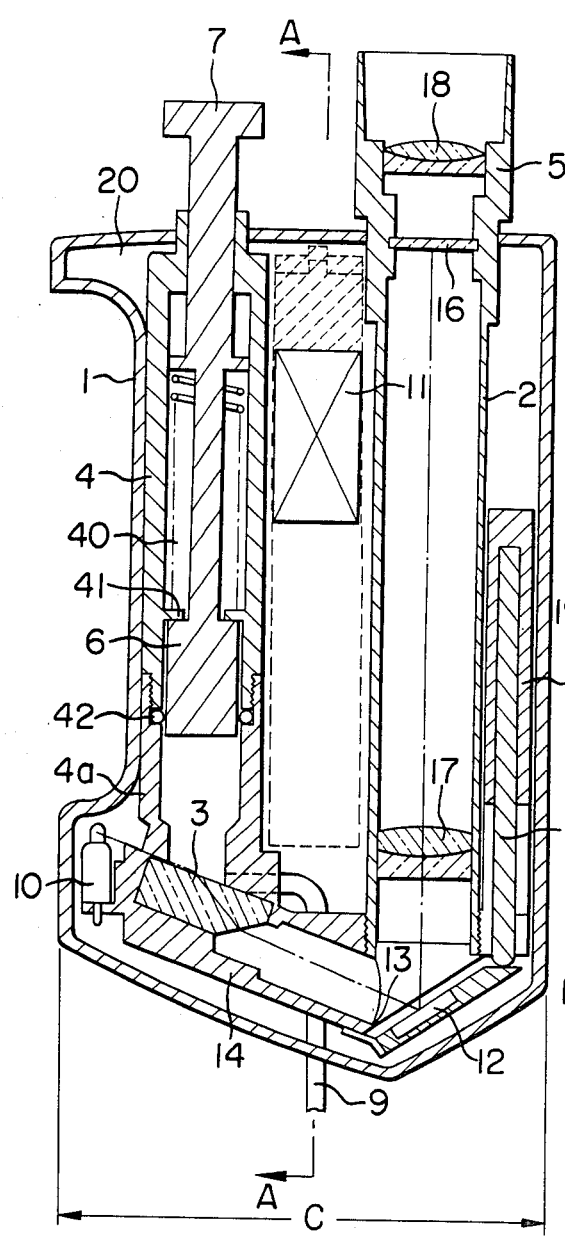
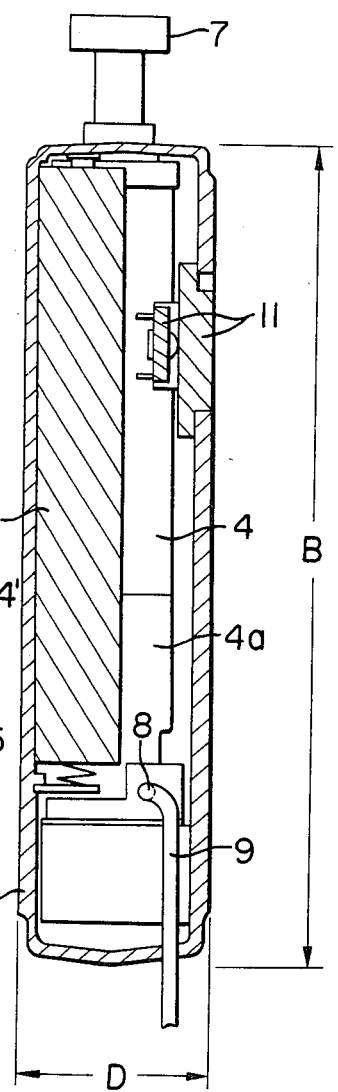

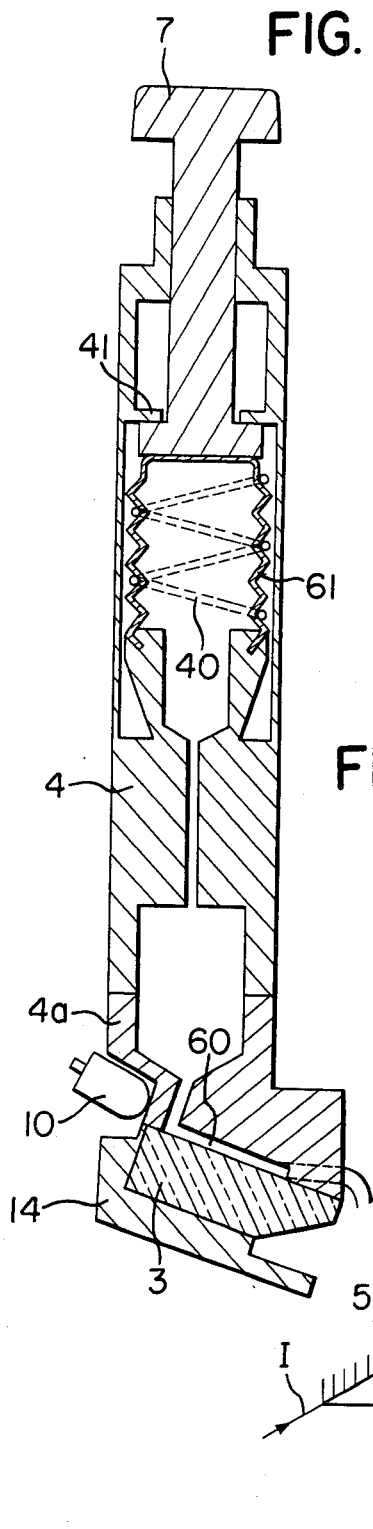
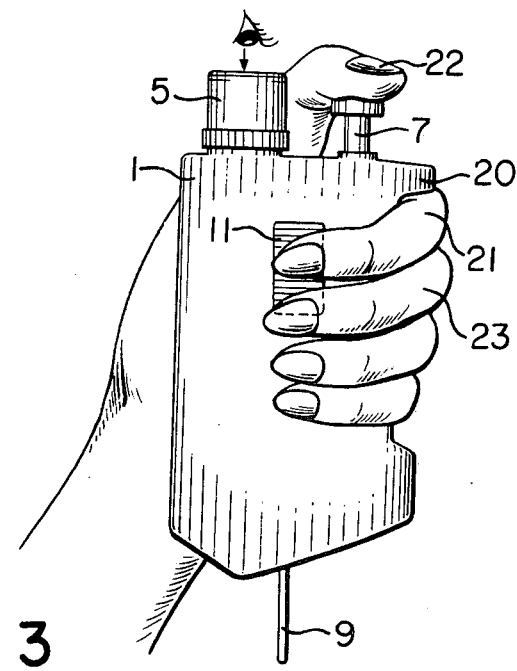
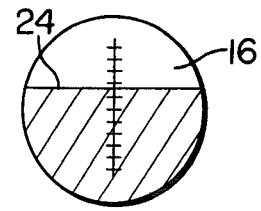
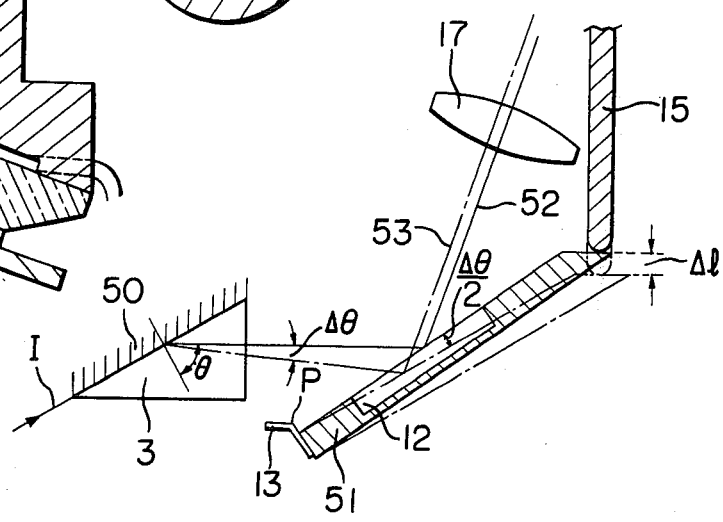

HANDY REFRACTOMETER

BACKGROUND OF THE INVENTION

1. Field of the Invention

This invention relates to a handy refractometer, and more particularly to a handy refractometer having a pump device.

2. Description of the Prior Art

Handy refractometers are known in which a sample is dropped onto the surface of a prism and a transparent cover is placed thereover to spread the sample over the prism surface, whereafter the sample is illuminated by ambient light and the critical angle of the sample is measured. However, with such refractometers, the measurer had to carry out the cumbersome procedures of introducing the sample by the use of a pipette and dropping it onto the prism each time the measurement was effected. Also, there are refractometers having a pump device to eliminate the disadvantage peculiar to such type of handy refractometers, but they are large and weighty and not portable. Further, there have been proposed portable refractometers having a pump device, but these are pistol-shaped and poor in portability and complicated in construction.

SUMMARY OF THE INVENTION

It is an object of the present invention to provide a handy refractometer having a pump device and which is compact and readily portable as well as simple in construction.

The invention will become fully apparent from the detailed desciption of some embodiments thereof taken in conjunction with the accompanying drawings.

BRIEF DESCRIPTION OF THE DRAWINGS

FIG. 1 is a cross-sectional view showing an embodiment of the present invention.

FIG. 2 is a cross-sectional view taken along line A—A of FIG. 1.

FIG. 3 illustrates a scale plate.

FIG. 4 illustrates the operation of the refractometer according to the present invention.

FIG. 5 illustrates the action of the FIG. 1 embodiment.

FIG. 6 shows another example of the pump device and prism used with the present invention.

DESCRIPTION OF THE PREFERRED EMBODIMENTS

FIG. 1 is a cross-sectional view of an embodiment of the present invention, and FIG. 2 is a cross-sectional view taken along line A—A of FIG. 1. Within a substantially rectangular, short, parallelopiped frame member 1 on the order of the length B, the width C and the thickness D, an observation lens barrel 2 and a cylinder 4, having its lower end sealed by a surface of a prism 3, are disposed in such a manner that the lengthwise directions of the lens barrel 2 and the cylinder 4 are coincident with the direction of the length A of the frame member 1. An eyepiece portion 5 is provided at one end of the observation lens barrel 2 and projected from the frame member 1. A piston 6 slidable in the cylinder 4 has an operating knob 7 integrally coupled thereto, and this knob 7 is projected from the frame member 1 in such a manner that it is in juxtaposed relationship with the eyepiece portion 5. To facilitate looking into the eyepiece portion 5, the operating knob 7 is designed such that the end thereof lies at a position lower than the end of the eyepiece portion 5. The piston 6 is biased by a compression spring 40 in a direction to increase the internal volume of the cylinder 4 and the upward movement of the piston is blocked by a flange 41 provided within the cylinder 4. The air-tightness in the cylinder 4 is maintained by an O-ring 42. The lower portion 4a of the cylinder 4 is formed of transparent plastic and has an opening 8 therein as shown in FIG. 2. A tube 9 connects the interior of the cylinder 4 to the outside and one end of the tube is connected to the opening 8 and the other end is projected out of the frame member 1. A light source 10 is provided adjacent to the transparent portion 4a of the cylinder 4, and may be turned on and off through an unshown line by manually closing and opening a switch 11. A mirror 12 is a light-path change-over mirror for directing the light from the prism 3 to the observation lens barrel 2. In the present embodiment, the mirror 12 is secured to a holding member 14 for the prism 3 by a plate spring 13 and is urged against a thermally expansible member 15 by the force of the spring 13. The thermally expansible member 15 is secured to a member 14' having its end connected to the holding member 14. Thus, the elongation of the thermally expansible member 15 corresponds to the temperature of the holding member 14, namely, the sample on the prism. By the expansion and contraction of the thermally expansible member 15, the mirror 12 is rotated, whereby the mirror 12 displaces the light beam from the prism 3 and effects temperature compensation. The details thereof will later be described in conjunction with FIG. 5. The observation lens barrel 2 is provided with a scale plate 16. A scale is formed on the scale plate 16 as shown in FIG. 3, and this scale has divisions of refractive indices and densities. The light beam from the prism 3 is reflected by the mirror 12, whereafter it is focused on the scale plate 16 by an objective lens 17. The scale of the scale plate 16 can be looked at through an eyepiece 18. As shown in FIG. 2, a power supply battery 19 is inserted in the space between the observation lens barrel 2 and the cylinder 4. The frame member 1 is of a rounded, rectangular, parallelopiped form so that it can be easily carried by a single hand, and the frame member is formed with a finger-engaging projection 20 so as to prevent the frame member 1 from slipping out of the hand when it is held by the hand.

With such a construction, the frame member 1 is carried by the left hand as shown in FIG. 4, and the index finger 21 is engaged with the projection 20, whereafter the operating knob 7 is depressed by the thumb 22. Thereupon, the volume in the cylinder becomes minimum. Then, the end of the tube 9 is immersed into the sample, whereafter the hand is released from the operating knob 7, whereupon the piston is moved upwardly by the force of the spring so that the sample is introduced into the cylinder 4. A switch 11 lies under the index finger 21 or the middle finger 23 and when the switch 11 is depressed by one of these fingers, the light source is turned on so that the black and white borderline 24 imaged on the scale plate 16, as shown in FIG. 3, can be viewed through the eyepiece portion 5. By reading the division through which the borderline passes, it is possible to know the refractive index of the sample. Thereafter, when the operating knob 7 is depressed, the sample which has been measured is discharged. The sample can be quickly discharged because the prism surface is inclined toward the opening as shown in FIG. 1.

Reference is now had to FIG. 5 to describe the operations of the mirror 12, the spring 13 and the thermally expansible member 15. The actual movement is considerably smaller than that shown. As the ambient temperature is varied, the refractive index of the sample 50 on the prism 3 is varied, so that the direction of the light beam from the prism 3 corresponding to the incident light beam I is inclined by $\Delta\theta$. On the other hand, the thermally expansible member 15 is elongated by $\Delta l$ with the variation in ambient temperature and rotates the mirror holder 51 by $\Delta\theta/2$ about the pivot P. Therefore, the light beam reflected by the mirror 12 becomes a light beam 53 parallel to the light beam 52 at the standard temperature and thus, the boundary between the light and dark on the scale (FIG. 3) always represents the refractive index at the standard temperature irrespective of the variation in ambient temperature.

Reference is now had to FIG. 6 to describe another example of the connection between the pump device and the prism. In FIG. 6, the members functionally similar to those in FIG. 1 are given similar reference numerals and need not be described.

A space 60 for receiving the sample is defined by the surface of the prism 3 and the transparent portion 4a, and the space 60 is connected to the interior of the cylinder 4 by a narrow passage. The introduction and discharge of the sample into and from the space 60 is accomplished by the expansion and contraction of bellows 61. In the present embodiment, the space 60 for receiving the sample is defined so that the non-uniformity of the sample created immediately after introduction is decreased. Also, the use of the bellows 61 makes the operation of the operating knob 7 lighter than in the embodiment of FIG. 1 because the force exerted during the depression of the operating knob 7 is only the restitutional force of the spring 40.

We claim:

1. A refractometer of the type in which a sample is introduced onto a prism by a pump device, whereafter the sample is illuminated so that the critical angle of the sample is measured, said refractometer comprising:
   a substantially rectangular parallelopiped frame member of relatively short length, width and thickness thereof;
   a cylinder provided within said frame member in such a manner that the longitudinal axis of the cylinder is parallel to that of said frame member, a piston being slidably disposed at the upper end of said cylinder, the end of said piston being projected from said frame member;
   an observation lens barrel disposed laterally within said frame member and in juxtaposed relationship with said cylinder, said lens barrel having an eyepiece portion which is projected from said frame member so as to be in juxtaposed relationship with the end of said piston;
   prism holding means for holding said prism adjacent to the lower end of said cylinder within said frame member; and
   reflector means for directing a light beam emergent from said prism to said observation lens barrel.

2. A refractometer according to claim 1, wherein: said reflector means includes a mirror and correction means for varying the inclination of said mirror in accordance with temperature variation.

3. A refractometer according to claim 2, wherein: said correction means includes:
   support means for supporting said mirror for rotation about a pivot point; and
   a thermally expansible member deformable with a temperature variation from a standard temperature, the deformation of said thermally expansible member causing said support means to rotate said mirror about said pivot point.

4. A refractometer according to claim 3, wherein: said support means includes a spring having one end secured to one end of said mirror and the other end secured to a portion of said refractometer; said thermally expansible member has one lengthwise end secured to a member connected to said prism holding means and the other lengthwise end in contact with the other end of said mirror; and, said spring urges said mirror against said thermally expansible member so as to rotate said mirror following the deformation of said thermally expansible member.

5. A refractometer according to claim 1 or 2, wherein: said prism holding means is integrally formed with said cylinder.

6. A refractometer according to claim 5, wherein: the lower surface of said cylinder is formed by the surface of said prism; the portion of said cylinder which is adjacent to the lower end thereof is transparent; and, said light source illuminates the sample through said transparent portion of said cylinder.

7. A refractometer according to claim 6, wherein: said cylinder and said observation lens barrel are disposed with a predetermined spacing therebetween sufficient to allow insertion of a battery for said light source.

* * * * *

UNITED STATES PATENT AND TRADEMARK OFFICE
CERTIFICATE OF CORRECTION

PATENT NO. : 4,243,321
DATED : January 6, 1981
INVENTOR(S) : MINORU OKUDA, et al.

It is certified that error appears in the above-identified patent and that said Letters Patent are hereby corrected as shown below:

In the headnote, after "[22] Filed: Aug. 27, 1979"

insert  --[30] Foreign Application Priority Data

Aug. 29, 1978 [JP] Japan............53-104472--

Signed and Sealed this

Fourteenth Day of April 1981

[SEAL]

Attest:

RENE D. TEGTMEYER

Attesting Officer

Acting Commissioner of Patents and Trademarks